United States Patent [19]

Antich et al.

[11] Patent Number: 5,236,694
[45] Date of Patent: Aug. 17, 1993

[54] 19F LABELLED DEXTRANS AND ANTIBODIES AS NMR IMAGING AND SPECTROSCOPY AGENTS

[75] Inventors: Peter P. Antich, Richardson; Padmakar V. Kulkarni, Dallas, both of Tex.

[73] Assignee: The Board of Regents, The University of Texas System, Austin, Tex.

[21] Appl. No.: 482,879

[22] Filed: Feb. 21, 1990

[51] Int. Cl.$^5$ .................... G01N 24/08; A61K 37/00; A61K 31/02; C08B 37/02

[52] U.S. Cl. ........................ 424/9; 436/173; 436/806; 128/653.4; 514/12; 514/59; 514/459; 514/743; 514/832; 549/417; 536/51; 536/112; 530/387.1

[58] Field of Search ............... 424/5, 9; 436/173, 806; 128/653.4, 654; 514/832, 743, 459, 12, 59; 549/417; 536/51, 112; 530/387.1

[56] References Cited

U.S. PATENT DOCUMENTS

| | | | |
|---|---|---|---|
| 4,586,511 | 5/1986 | Clark, Jr. | 128/653.4 |
| 4,612,185 | 9/1986 | Dean | 424/2 |
| 4,631,190 | 12/1986 | Shen | 424/85 |
| 4,639,364 | 1/1987 | Hoey | 424/9 |
| 4,640,833 | 2/1987 | Tamborski | 424/85 |
| 4,741,900 | 5/1988 | Alvarez | 424/85 |
| 4,838,274 | 6/1989 | Schweighardt | 128/654 |
| 5,080,885 | 1/1992 | Long | 424/5 |
| 5,116,599 | 5/1992 | Rogers et al. | 424/9 |

FOREIGN PATENT DOCUMENTS 0186947 4/1987 European Pat. Off. .
WO89/02931 4/1989 PCT Int'l Appl. .

OTHER PUBLICATIONS

Ackerman et al, "NMR Thermal Imaging," Scientific Program, S.M.R.M., Third Annual Meeting, p. 1 (1984).
Dieckman et al, Abstract, "$^{19}$F NMR Thermal Imaging Utilizing Perfluorocarbons", S.M.R.M., Sixth Annual Meeting, p. 815 (Aug. 17-21, 1987).
Kirschenlohr, "Ca$_{2+}$ Transient, Mg$^{2+}$ and pH Measurements in Cardiac Cycle by $^{19}$F NMR", Proc. Nat'l Acad. Sci. USA, 85(23):9017-9021 (1988).
Derwent Abstract No. 88-195824 (Asahi Kasei Kogyo, 7 Jun. 1988).
Brauer, Biochemistry 25:2187-2191 (1986).
Miura, Biochemical and Biophysical Research Communications 110:406-411 (1983).
Fishman, Magnetic Resonance Imaging 5:279-285 (1987).
Ratner, Magnetic Resonance in Medicine 5:548-554 (1987).
Ratner, Investigative Radiology 23:361-364 (1988).
Taylor, Biophysical Journal 43:261-267 (1983).
Deutsch, "Intracellular pH as Measured by $^{19}$F NMR" (1987).
Taylor, Biophysical Journal 53:227-233 (1988).
Levy, "Synthesis and Characterization of $^{19}$NMR Chelators for Measurement of Cytosolic Free Ca," C441-C449 (1987).
Metcalfe, Cell Calcium 6:183-195 (1985).
Smith, Biochimica et Biophysica Acta 889:72-73 (1986).
Evers, Biochemical and Biophysical Research Communications 151:1039-1045 (1988).
Hull, NMR in Biomedicine 1:11-19 (1988).
Shimizu, Magnetic Resonance in Medicine 5:190-295 (1987).
Levy, Biochimica et Biophysica Acta, 310:398-405 (1973).
Wolfrom, Carbohydrate Research 11:63-76 (1969).
Goldberger, Biochemistry 1:401-405 (1962).
Schallenberg, Journal of the American Chemical Society 777:2779-2783 (1955).

Primary Examiner—Glennon H. Hollrah
Assistant Examiner—Gary E. Hollinden
Attorney, Agent, or Firm—Arnold, White & Durkee

[57] ABSTRACT $^{19}$F labelled compounds are disclosed which are useful in methods of NMR imaging and spectroscopy. The compounds comprise a $^{19}$F-containing sensor moiety, and a transport polymer or substrate, and can optionally also comprise a spacer moiety to separate the sensor moiety and the transport polymer.

8 Claims, No Drawings

19F LABELLED DEXTRANS AND ANTIBODIES AS NMR IMAGING AND SPECTROSCOPY AGENTS

BACKGROUND OF THE INVENTION

Nuclear magnetic resonance (NMR) techniques are finding increasing use in medical diagnostics. NMR imaging, or magnetic resonance imaging (MRI) as it is sometimes known, has been found to be useful in the detection of a variety of diseases and disorders. MRI has several advantages over other imaging techniques. For example, unlike computerized tomographic methods, MRI does not employ ionizing radiation, and therefore is believed to be safer. Also, MRI can provide more information about soft tissue than can some other imaging methods.

The majority of the NMR techniques developed so far have been based on imaging of hydrogen nuclei. However, other nuclei offer potential advantages with respect to NMR. $^{19}F$ in particular is of interest. The fluorine nucleus offers a strong NMR signal magnitude (high gyromagnetic ratio) second only to that of protons. Virtually no imagable fluorine exists naturally in the human body, so no background signal exists; any detectable signal comes only from whatever $^{19}F$ has been administered to the subject.

$^{19}F$ is a stable isotope and is naturally abundant, so there is no need for isotopic enrichment. Because its gyromagnetic ratio is about 94% that of hydrogen, existing equipment designed to image protons can be inexpensively adapted for $^{19}F$.

Although $^{19}F$ NMR has potential benefits, there is a need for new and improved $^{19}F$-containing agents which can be used in NMR imaging and spectroscopy techniques.

SUMMARY OF THE INVENTION

The present invention relates to $^{19}F$ labelled compounds which can be used as NMR imaging and spectroscopy agents. In one aspect of the present invention, such a compound comprises a transport polymer and a $^{19}F$-containing sensor moiety, and may optionally also include a spacer moiety separating the $^{19}F$-containing sensor moiety and the transport polymer. Because the $^{19}F$ nucleus is very sensitive to changes in its steric and electronic environment, the compound can be used to sense different tissue parameters and cell properties.

The transport polymer can provide multiple substitution sites, allowing more $^{19}F$-containing sensor moieties to be attached, and thereby making the signal produced by the compound easier to detect. The polymer or substrate serves the multiple purposes of anchoring the sensor moiety, targeting it, and reducing its toxicity. As to the anchoring function, the bonding can be chosen so as to keep the sensor moiety attached to the substrate, for microenvironmental monitoring, or permitting the sensor to detach and reach the interior of cells, for intracellular monitoring. The targeting function is based on the specificity of the substrate. Where that specificity is based on the stereochemical characteristics of the substrate, that specificity will not be disturbed by (a) substitution of $^{19}F$ for H, because the atomic radius of the two are effectively the same, (b) substitution of $^{19}F$ for —OH because of similar size and electronegativity.

Other substrates to which $^{19}F$-containing sensor moieties can be attached include antibodies or fragments thereof, enzymes, receptor binding agents, and a variety of other biologically compatible substances.

In one embodiment of the present invention, the $^{19}F$-containing sensor moiety is bonded to a spacer moiety, which is bonded to the transport polymer or substrate. The spacer moiety can be used to isolate the $^{19}F$ atoms from the substrate, thereby enhancing the NMR signal produced. The spacer moiety preferably contains an amino group, has a chain length of approximately 1-100 C atoms, and can optionally include one or more $^{19}F$ atoms. Suitable spacer moieties include alkyl, alkoxy, and alkaryl hydrocarbons which contain a primary amine group, hydrazine, hydrazide, semicarbazide, hydroxylamine, or aminophenyl.

In another embodiment of the present invention, the $^{19}F$-containing sensor moiety is directly bonded to the substrate or transport polymer. For example, metabolically important substrates can be directly fluorinated and used as indicators of particular disorders.

The present invention also relates to methods of using $^{19}F$-labelled compounds in methods of $^{19}F$ magnetic resonance imaging (MRI) or magnetic resonance spectroscopy (MRS). Such methods comprise administering to a living subject an effective amount of a $^{19}F$-labelled compound as described above, and then detecting the $^{19}F$ NMR signal produced thereby. The compound contains an amount of $^{19}F$ effective to provide a detectable NMR signal.

Fluorinated compounds in accordance with the present invention have both diagnostic and prognostic uses, and can serve as physiological probes and cell-function reporters. They can be used not only to delineate tissues at risk and to characterize disease states, but also for monitoring the results of therapy. Specific uses for such compounds include vascular imaging, tumor imaging, and detection of lesions in atherosclerosis, bone metastases, and myocardial infarction. Among the physiologically important parameters that could be sensed are oxygen content, temperature, pH, and the concentration of ions such as $Na^+$, $Ca^{2+}$, and $Mg^{2+}$.

DETAILED DESCRIPTION OF SPECIFIC EMBODIMENTS

A wide variety of transport polymers or substrates can be used in the present invention. Suitable examples include dextran polymers, aminodextrans, cyclodextrins, polylysine, polyaspargine, dextrin inclusion compounds of various sizes, highly charged molecules such as dextran sulfate, heparin, and heparin sulfate, other biocompatible polysaccharides such as hyaluronic acid or carboxymethylcellulose, polylactic acid, polyglycolic acid, and polymers synthesized by polymerizing fluorinated glucose and other sugar molecules. If, for example, the transport polymer is aminodextran, it can suitably have a molecular weight between about 100d and about 500 Kd.

When the polymer is itself fluorinated, it can be attached to a variety of other agents, such as polyclonal or monoclonal antibodies or fragments thereof, receptor binding agents, histochemicals, enzymes, hormones, antibiotics, antiviral agents, antitumor agents, proteins, or a variety of other biological substances.

Among the suitable $^{19}F$-containing sensor moieties are simple fluorinated alkyls such as $CH_2F$, $CHF_2$, $CF_3$, fluorinated acetates such as $COCH_2F$, $COCHF_2$, and $COCF_3$, as well as fluoroaniline (useful for sensing pH), fluorinated pyrophosphate analogs such as fluoroalkyl phosphonates, fluorinated polyamines, fluorinated porphyryns and their metal complexes, fluorinated histochemicals, and fluorinated biotin or avidin.

Methods of fluorination in accordance with the present invention can suitably be by one of the following methods.

The hydroxyl groups of a polymer can be replaced by $^{19}F$ atoms, using chemical, enzymatic, or a combination of chemical and enzymatic methods. Partial hydroxyl replacement can be accomplished by using diethylaminosulfur trifluoride (DAST) as a fluorinating agent.

Alternatively, CHO groups on the polymer can be replaced by $^{19}F$ using DAST.

As another option polymeric hydroxyl groups can be esterified, for example:

polymer-OH + $C_2F_5COOCOC_2F_5$ → polymer-OCOCF$_2$CF$_3$ polymer-OH + ClCOC$_2$F$_5$ → polymer-OCOCF$_2$CF$_3$ polymer-OH + CF$_3$COOCOCF$_3$ → polymer-OCOCF$_3$ polymer-OH + ClCOCF$_3$ → polymer-O-COCF$_3$ Also, hydroxyl groups could be oxidized using reagents such as periodate, and then coupled to the amino groups of $^{19}F$-labelled compounds, then reduced with reagents such as NaBH$_4$.

Polymer hydroxyl groups could be activated by cyanogen bromide and then coupled to a fluorinated amine, yielding an iminocarbonic acid ester.

Polymer hydroxyl groups, such as in a dextran polymer, can be utilized to form 3-bromo-2-hydroxyl propyl dextrans, which can be transformed into epoxide derivatives. The epoxide derivative is highly reactive and in alkaline solution at room temperature can be coupled with substances containing nucleophilic groups like alkyl and aryl primary amines, hydroxyl groups, and thiol groups. For example:

dextran(OH)$_3$ + 3-bromo-2-hydroxyl propyl epoxide →

3-bromo-2-hydroxy propyl dextran

Rxn with NaOH → dextran with epoxide

Rxn with RAH → dextran-OCH$_2$CHOHCH$_2$AR

A = O, S, NH
R = organic fluorine-containing moiety

Fluorinated amines can be attached to polysaccharides. For instance, carboxymethyl-cellulose can be esterified to produce the methyl ester which, on treatment with hydrazine hydrate, forms hydrazide. The hydrazide on diazotization with HCl and NaNO$_2$ forms a reactive azide. The azide in alkaline solution will react rapidly with amines to form the covalently bonded product polymer-CONHR, where R is a fluorinated aliphatic or aromatic amine.

CMCOOH + CH$_3$OH + NH$_2$NH$_2$ → CMCOHNNH$_2$

Rxn with NaNO$_2$ + HCl → CMCON$_3$

Rxn with RNH$_2$ → CMCONHR

Aminodextrans can be fluorinated using S-ethyl thiol trifluoroacetate (SETFA) as a fluorinating agent. Acylation of available amino groups can be accomplished by using an excess of SETFA as the acylating reagent.

Alternatively, amino groups can be acylated using acid fluorides (anhydrides).

D-NH$_2$ + (CF$_3$CF$_2$CO)$_2$O → D-NHCOCF$_2$CF$_3$

D-NH$_2$ + ClCO-AR → D-NHCO-AR

AR = aromatic ring containing F

D-NH$_2$ + ClCO-AR-LF$_3$ → D-NHCO-AR-LF$_3$

AR = aromatic ring
L = alkyl chain

Other possible reactions include acylation using fluorinated propionic anhydride, succinic anhydride (for example - trifluoroacetamido succinic anhydride) reactions with fluorinated phenyl isothiocyanate, and reactions with fluorinated alkyl isothiocyanate.

Where antibodies or fragments thereof are used, the sensor moieties can be selectively attached to sites not directly involved in antibody-antigen binding, thereby allowing the antibody to retain its immunoreactivity. Possible sites for attachment include carbohydrate groups, amino groups, sulfhydryl groups, or combinations thereof.

The following specific examples illustrate the preparation of compounds in accordance with the present invention.

N-Trifluoroacetamide D-Glucose

Glucoseamine in anhydrous methanol was treated with s-ethyl thiol trifluoroacetate (SETFA) as described by Wolform and Conigliaro, Carbohydrate Research, 11, 63 (1969). A suspension of 2-amino-deoxy-D-glucose hydrochloride (10 g) in 50 ml anhydrous methanol was treated with an equivalent amount of sodium methoxide in methanol (1.06 g of Na in 10 ml methanol). The mixture was stirred (magnetic stirrer) till a clear solution was obtained. NaCl precipitate remained at the bottom. To this, SETFA (10 g) was added. The reaction mixture was stirred at room temperature for 24 hrs. The solution was evaporated to a solid residue and the residue was extracted with hot acetone. Ether was added to the cooled acetone extract and the mixture was refrigerated overnight. The white crystalline compound was recrystallized from a mixture of acetone-ether to obtain shiny crystals.

| Results Yield: 8.2 g. MP: 193-195° C. Analysis | | | | |
|---|---|---|---|---|
| Element: | C | H | N | F |
| Calculated: | 34.92 | 4.40 | 4.09 | 20.72 |
| Found: | 36.89 | 4.75 | 4.92 | 20.75 |

The product was soluble in water. Elemental analysis data were in agreement with the calculated values.

Proton and F-19 NMR data confirmed the formation of N-trifluoroacetamido-D-glucose.

2-deoxy-glucose NH$_2$HCl + SETFA $\xrightarrow{\text{MeONa in MeOH}}$ 2-deoxyglucose-NH—COCF$_3$.

Trifluoroacetyl-DL-Lysine

Trifluoroacetyl-DL-lysine was obtained by treating DL-lysine monohydrochloride with s-ethyl thiol trifluoro acetate (SETFA) in basic solution, as described in Schallenberg and Calvin, JACS 77, 2779 (1955).

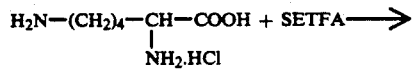

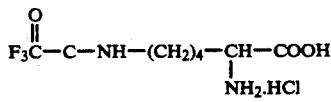

SETFA (4.0 ml) was added to DL-lysine monohydrochloride 3.6 g (20 mmol), dissolved in 20 ml of 1N NaOH. The heterogeneous mixture was stirred for 6 hours at room temperature and cooled for 1 hour in an ice cold water bath. The solid that separated was filtered and washed with cold water. It was recrystallized from ethanol.

Results

Yield: 0.8 g (16%) (Loss of product due to washing with cold water).
MP: 262°-263° C.
H-1 NMR: 3.82 δ CH; J=1.5, 1.7, 1.96, 3.41 (Solvent D$_2$O).
F-19 NMR: Sharp signal (solvent D$_2$O).

| Elemental Analysis: | C | H | N | F |
|---|---|---|---|---|
| Found: | 39.87 | 5.45 | 11.61 | 23.52 |
| Calculated: | 39.67 | 5.41 | 11.57 | 23.55 |

Aminodextrans

Aminodextrans (molecular weight: 10k, 40k, and 70k) were obtained from Molecular Probes, Inc., Portland, Oreg.

| Molecular Size | Number of amino groups per molecule |
|---|---|
| 10k | 6.8 |
| 40k | 13 |
| 70k | 30 |

Aminodextran molecule was reacted with s-ethyl thioltrifluoracetate (SETFA) in a formamide and pyridine mixture to yield a product in which the amino groups of the aminodextrans were modified with trifluoracetyl moiety, as described in Goldberg and Anfinsen, Biochem., 1, 401 (1962).

The general synthesis procedure was as follows: Aminodextran was dissolved in formamide and pyridine (2:1 v/v). S-ethylthioltrifluoroacetate (SETFA) was added slowly with stirring. The mixture was stirred overnight. The desired product was precipitated with cold ethanol and further purified by dialysis against water, and the powdered product obtained by lyophilization.

As a specific example, aminodextran 70k (0.6 g) was dissolved in 10 ml formamide by stirring for 2-3 hours. Pyridine 5 ml was added, and stirring continued until the homogeneous solution was obtained. The pH was approximately 7 by paper. S-ethylthioltrifluoroacetate 3 ml was added dropwise for a period of 30 minutes with vigorous stirring. This reagent is immiscible with the above solvent system. However, it forms small droplets and slowly undergoes reaction which could be seen by the fall in pH values and homogeneity of the solution. The mixture was stirred overnight and poured on chilled (−12° C.) absolute ethanol (150 ml) with vigorous stirring. The white precipitate obtained was held at −12° C. for an additional 4 hours with stirring. The precipitated product was centrifuged and washed with ethyl alcohol. The product was dissolved in distilled water and dialyzed against distilled water for 24 hours with 6 changes using 1000 ml of water each time. The dialyzed solution was centrifuged and the clear solution was lyophilized to obtain a white silky solid.

Yield: 0.56 g
TLC Matrix: silica gel 60A, MK6F, Whatman
Solvent: Pyridine/acetic/acid water (9:1:90, v/v/v)
Detection: 50% H$_2$SO$_4$
R$_f$ of starting material: 0.41
R$_f$ of final product: 0.74
Proton NMR spectra: Typical polymeric appearance
F-19 NMR spectra: Single (Fluorine) sharp signal

| Elemental Analysis | C | H | N | F |
|---|---|---|---|---|
| Calculated*: | 43.87 | 5.94 | 1.11 | 2.88 |
| Found: | 40.65 | 5.78 | 0.62 | 2.26 |

*percentages of elements calculated by assuming the molecular weight of dextran to be 70k.

Results

Trifluoroacetylated aminodextran 10K and 40K:

| 10K: | TLC analysis: Solvent system: pyridine/acetic acid/H$_2$O (9:1:90) |
|---|---|
| | R$_f$ of starting material: 0.5 |
| | R$_f$ of final product: 0.84 |
| NMR spectra analysis: | Proton spectra: Typical polymeric compounds (D$_2$O) |
| | F-19 spectra: Single fluorine, sharp signal |
| (D$_2$O) | |

| Elemental analysis: | C | H | N | F |
|---|---|---|---|---|
| Found: | 40.01 | 5.65 | 0.83 | 2.50 |
| Calculated*: | 43.56 | 5.81 | 1.39 | 4.13 |

*percentages of elements calculated by assuming the molecular weight of dextran to be 10K.

Trifluoacetylation of Poly-L-Lysine

General Procedure:

Trifluoroacetylation of poly-L-lysine is carried out with S-ethyl thioltrifluoroacetate in dimethylformamide, as described in Levy and Paselk, Biochem. Biophys. Acta, 310, 398–405 (1973). The amino groups of poly-L-lysine are modified with the trifluoroacetyl moiety.

Poly-L-lysine.HBr (molecular weight 8,800) was reacted with S-ethyl-thioltrifluoroacetate in dimethylformamide. Poly-L-lysine.HBr (100 mg, 11.36 μmoles)

was dissolved in 20 ml of DMF with stirring, for 30 minutes when an almost clear solution was obtained. Triethylamine (TEA) 50 μl was added (appearance of precipitate noted) and the stirring continued for 15 minutes. S-ethylthioltrifluoroacetate (SETFA 51.737 mg, 327.17 μmoles), dissolved in 1 ml of DMF, was added dropwise to the reaction mixture with constant stirring for 15 minutes. The pH was adjusted after each addition of SETFA. A clear solution obtained at the end, was stirred for another 90 minutes and then poured onto chilled absolute ether. The solution was decanted. The precipitate was centrifuged and then dissolved in 15–20 ml water and dialyzed against distilled water at 4° C. for 48 hours. The shiny powdery product was obtained by lyophilization of the dialyzed solution.

Results

Yield: 20 mgs

F-19 NMR spectra: A sharp single fluorine signal ($D_2O$)

Trifluoroacetamido-succinylated Poly-L-Lysine: Poly-L-Lysine (50 mg, 5.68μ Mol) in 20 ml phosphate buffer (pH=7.24) was reacted with (120 mg) trifluoroacetamidosuccinic anhydride for 30 minutes. General procedure for preparation of succinylated Poly-L-Lysine is described by W. B. Stason, M. Vallotton and E. Haber; Biochem. Biophys. Acta. 133:582–584 (1967). The product was purified by exhaustive dialysis against d. water and lyophilized to obtain white solid.

One way of producing a stronger signal from trifluoroacetylated aminodextrans would be to trifluoroacetylate the hydroxyl groups instead of the amino groups, which will dramatically increase the number of available sites, and therefore increase the concentration of $^{19}F$ in the molecule. The in vivo NMR signal can also be optimized by using spacer moieties to separate the $^{19}F$ from the substrate.

In the NMR methods of the present invention, the $^{19}F$-labelled compound is administered to a living subject, preferably parenterally or orally. They can suitably be administered in a formulation containing one or more of the $^{19}F$-labelled compounds and a pharmaceutically acceptable diluent or carrier.

The preceding description is intended to illustrate specific embodiments of the present invention, not to provide an exhaustive description of all possible embodiments of the invention. Persons skilled in this field will recognize that modifications could be made to the preceding examples which would still be within the scope of the present invention.

We claim:

1. A method of NMR imaging or spectroscopy, comprising the steps of administering to a living subject a $^{19}F$ labelled NMR agent, the NMR agent comprising (a) a transport polymer selected from the group consisting of dextran polymers and aminodextrans, having a molecular weight between approximately 100 d and 500 kd, and antibodies and fragments thereof, and (b) a $^{19}F$-containing sensor moiety selected from the group consisting of fluorinated alkyls, fluorinated acetates, fluoroaniline, and fluoroalkyl phosphonates, in an amount effective to provide a detectable NMR signal; and then detecting the $^{19}F$ NMR signal produced thereby.

2. A method of NMR imaging or spectroscopy, comprising the steps of administering to a living subject a $^{19}F$ labelled NMR agent, the NMR agent comprising a transport polymer selected from the group consisting of dextran polymers and aminodextrans, having a molecular weight between approximately 100 d and 500 kd, and a $^{19}F$-containing sensor moiety selected from the group consisting of fluorinated alkyls, fluorinated acetates, fluoroaniline, and fluoroalkyl phosphonates, in an amount effective to provide a detectable NMR signal; and then detecting the $^{19}F$ NMR signal produced thereby.

3. A method of NMR imaging or spectroscopy, comprising the steps of administering to a living subject a $^{19}F$ labelled NMR agent, the NMR agent comprising a transport polymer selected from the group consisting of antibodies and fragments thereof capable of recognizing a tissue specific antigenic marker, and a $^{19}F$-containing sensor moiety selected from the group consisting of fluorinated alkyls, fluorinated acetates, fluoroaniline, and fluoroalkyl phosphonates, in an amount effective to provide a detectable NMR signal; and then detecting the $^{19}F$ NMR signal produced thereby.

4. The method of claim 1, 2, or 3, where the $^{19}F$ labelled NMR agent further comprises a spacer moiety having from approximately 1–100 carbon atoms, selected from the group consisting of alkyl, alkoxy, aryl, and alkaryl hydrocarbons which contain an amino group, hydrazine, hydrazide, semicarbazide, and hydroxylamine, with the $^{19}F$-containing sensor moiety and transport polymer being separately attached to the spacer moiety.

5. The method of claim 1, 2, or 3, further comprising the step of using the detected $^{19}F$ NMR signal for vascular or tumor imaging.

6. The method of claim 1, 2, or 3, further comprising the step of using the detected $^{19}F$ NMR signal for lesion detection.

7. The method of claim 1, 2, or 3, further comprising the step of using the detected $^{19}F$ NMR signal for measuring pH of tissue of the subject.

8. The method of claim 1, 2, or 3, further comprising the step of using the detected $^{19}F$ NMR signal for measuring oxygen content of tissue of the subject.

* * * * *

UNITED STATES PATENT AND TRADEMARK OFFICE
CERTIFICATE OF CORRECTION

PATENT NO. : 5,236,694

DATED : August 17, 1993

INVENTOR(S) : Peter P. Antich, et al

Page 1 of 2

It is certified that error appears in the above-indentified patent and that said Letters Patent is hereby corrected as shown below:

On the Title Page, Item [54], should read :

--$^{19}$F Labelled Compounds as NMR Imaging and Spectroscopy Agents--.

At column 2, lines 6-7, there should not be a paragraph break between "spacer" and "moiety".

At column 4, line 58, in the third column of data in table, under the heading "N", "4.09" should instead be --5.09--.

UNITED STATES PATENT AND TRADEMARK OFFICE
CERTIFICATE OF CORRECTION

PATENT NO. : 5,236,694
DATED : August 17, 1993
INVENTOR(S) : Peter P. Antich, et al It is certified that error appears in the above-indentified patent and that said Letters Patent is hereby corrected as shown below:

At column 6, line 57, please insert the following:

--40K:  TLC analysis:
Solvent system: pyridine/acetic acid/$H_2O$ (9:1:90)
$R_f$ of starting material: 0.48
$R_f$ of final product: 0.76

NMR spectra analysis:
Proton spectra: Typical polymeric ($D_2O$)
F-19 spectra: Single fluorine, sharp signal ($D_2O$)

Elemental analysis:

|  | C | H | N | F |
|---|---|---|---|---|
| Found: | 40.82 | 5.97 | 0.61 | 1.58 |
| Calculated*: | 43.92 | 5.98 | 0.99 | 2.35 |

*percentages of elements by assuming the molecular weight of dextran to be 40K.--

Signed and Sealed this

Nineteenth Day of April, 1994

BRUCE LEHMAN

Attest:

Attesting Officer

Commissioner of Patents and Trademarks